United States Patent [19]

Moyet-Ortiz

[11] Patent Number: 5,065,863

[45] Date of Patent: Nov. 19, 1991

[54] STERILE GLOVE PACKAGING AND METHOD OF PREVENTING CONTAMINATION FROM SPREADING FROM ONE ENVIROMENT TO ANOTHER

[76] Inventor: Francisco Moyet-Ortiz, Valle Tolimas, Calle 11 N-17, Caquas, P.R. 00625

[21] Appl. No.: 594,694

[22] Filed: Oct. 9, 1990

[51] Int. Cl.$^5$ .............................................. B65D 85/18
[52] U.S. Cl. .................................... 206/210; 206/278; 206/438
[58] Field of Search ............... 206/205, 210, 213, 278, 206/363, 438

[56] References Cited

U.S. PATENT DOCUMENTS

| | | | |
|---|---|---|---|
| 3,870,150 | 3/1975 | Hummel | 206/438 |
| 3,892,314 | 7/1975 | Semp | 206/363 |
| 3,923,577 | 12/1975 | Baab | 206/278 |
| 4,002,276 | 1/1977 | Poncy et al. | 206/278 |
| 4,069,913 | 1/1978 | Harrigan | 206/438 |
| 4,155,494 | 5/1979 | Poncy et al. | 206/278 |
| 4,159,069 | 6/1979 | Poncy et al. | 206/278 |
| 4,275,812 | 6/1981 | Poncy et al. | 206/278 |
| 4,773,532 | 9/1988 | Stephenson | 206/278 |
| 4,915,226 | 4/1990 | Keenan | 206/278 |
| 4,951,815 | 8/1990 | Ulbrich | 206/278 |

FOREIGN PATENT DOCUMENTS

| | | | |
|---|---|---|---|
| 0863737 | 2/1971 | Canada | 206/278 |
| 2206377 | 8/1973 | Fed. Rep. of Germany | 206/278 |
| 0984343 | 2/1965 | United Kingdom | 206/278 |

Primary Examiner—Jimmy G. Foster
Attorney, Agent, or Firm—William Nitkin

[57] ABSTRACT

A combination sterile glove and packaging wherein the glove is contained between a front cover and a rear cover with the edges of the covers releasably sealed with a glove compartment seal forming an upper compartment which is openable for insertion of the user's hand into the glove while the glove is still contained within the lower compartment amd when ready for use, the lower compartment is openable by peeling apart the front cover from the rear cover and separating the covers from the glove at the time that the glove is needed for use.

3 Claims, 2 Drawing Sheets

STERILE GLOVE PACKAGING AND METHOD OF PREVENTING CONTAMINATION FROM SPREADING FROM ONE ENVIROMENT TO ANOTHER

BACKGROUND OF THE INVENTION

1. Field of the Invention

The article of this invention resides in the area of sterile gloves and more particularly relates to a sterile glove with packaging to preserve its sterility until use and method of use of such glove and packaging to prevent contamination from spreading from one environment to another.

2. Description of the Prior Art

It is common practice to use sterilized gloves in medical procedures. It is desirable for such gloves, which are usually made of rubber or other similar materials, to be held within a sterilized package such as described in U.S. Pat. No. 4,099,614 to Heissenberger which patent discloses a package with various folds to contain the gloves therein before use.

SUMMARY OF THE INVENTION

It is an object of this invention to provide an improved sterile glove package which will maintain the glove in a sterile condition even while the user is placing it on his/her hand.

It is a further object of this invention to expose the glove to the environment immediately before actual usage, thus avoiding the problems associated with a sterile glove coming into contact with an unsterile environment and maximizing factors of cleanliness and sterility before medical procedures are performed.

The structure of this invention includes a medical glove of the rubber, latex or other equivalent material contained within a dual-compartment packaging having an upper entry compartment and lower glove compartment wherein the entry compartment is openable so that the user can gain access through the wrist section of the glove to insert the user's hand into the glove while the glove compartment surrounding the exterior of the glove still remains sealed thereby keeping the glove in a sterile state. The remainder of the packaging need only be removed from the glove immediately before usage so as to maintain the glove in a sterile state for as long as possible before use. The dual compartment packaging of this invention includes a glove compartment in which the glove is contained between a front and rear cover which covers are releasably sealed around their edges, such sealing extending substantially around the glove. The upper entry compartment's lower sealed edge is formed from the glove compartment's upper sealed edge. The upper entry compartment is also sealed around its edges with portions of the upper entry compartment's front entry cover and rear entry cover extending beyond the releasable seal separably to form tabs to pull apart to open the entry compartment. The tabs, when pulled apart, will tear the front entry cover from the rear entry cover along the sealed seams as will be described further below, exposing the wrist opening of the glove, the remainder of which glove is still sealed within the glove compartment. Once the hand is inserted in the glove and one desires to expose the sterile glove, one or an assistant can pull the tabs at the bottom of the glove compartment and peel the covers apart, separating the seams of the front glove compartment cover from the rear glove compartment cover which covers can be peeled back to the glove attachment members and the covers can be torn and removed from the gloves, leaving the glove on the wrist with merely the wrist sleeve of the glove beyond the wristband to be rolled up the user's arm as will be described further below. The glove can be used before the glove compartment is opened in one environment, and the glove compartment can be opened to expose the sterile glove in another environment.

BRIEF DESCRIPTION OF THE PREFERRED EMBODIMENT(S)

Figure 1:
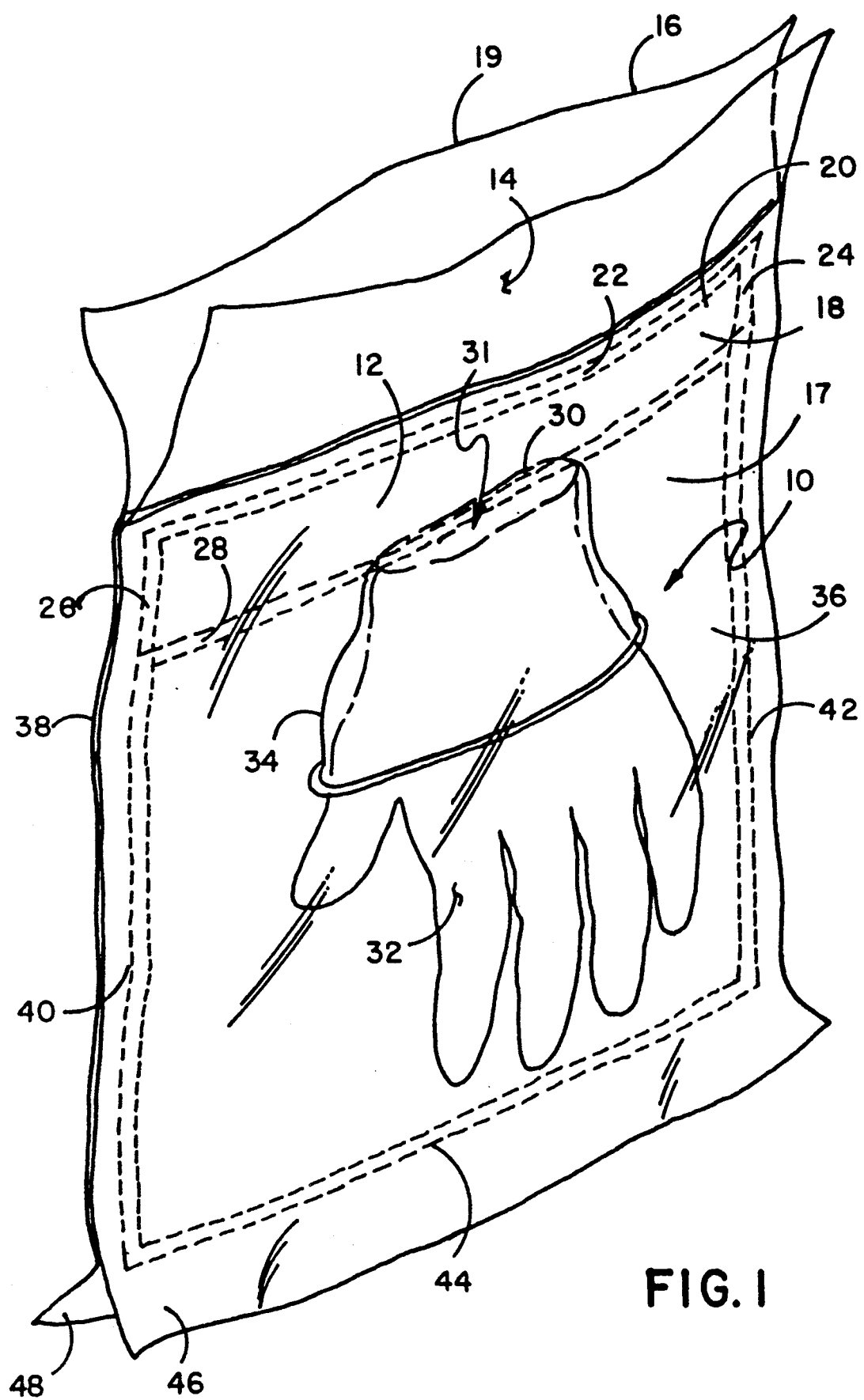
FIG. 1 illustrates a perspective view of the sterile glove and packaging of this invention.

FIG. 1 illustrates a perspective view of the sterile glove and packaging of this invention. Seen in this view is glove compartment 10 which contains glove member 32 between front glove compartment cover 36 and rear glove compartment cover 38. Sleeve 34 of glove 32 is rolled forward along glove 32 to wristband 31 and is attached to covers 36 and 38 as will be described below. An entry compartment 12 is disposed above open wrist band 31 of the glove which has an upper glove compartment seal 28 extending from the periphery of wristband 31 of the glove along the base of the upper entry compartment between front entry cover 18 and rear entry cover 20 which extend upwards a distance and have their outer edges sealed together by left entry seal 26 and right entry seal 24. At a point along the front and rear entry covers 18 and 20 is upper entry seal 22 which extends thereacross, joining front entry cover 18 to rear entry cover 20. Portions of front entry cover 18 extend further beyond upper entry seal 22 to form front entry tab 14, and portions of the rear entry cover 20 extend beyond upper entry seal 22 to form the rear entry tab 16. One can gain access to the area above the opening of the glove at wristband 31 by pulling apart front entry tab 14 and rear entry tab 16 to separate and break apart the separable upper entry seal 22, left entry seal 26 and right entry seal 24 all the way down to upper glove compartment seal 28. One can then insert one's hand through wristband 31 into glove 32. The exterior of glove 32 still within glove compartment 10 is not exposed to any exterior atmosphere and is therefore maintained in its sterile state. When one desires to expose the remainder of the glove to the atmosphere after having inserted one's hand into glove 32, for example, just before the glove is to be used, such as in an operative procedure, one can pull apart front glove compartment tab 46 and rear glove compartment tab 48 which are extensions, respectively, of the front glove compartment cover 36 and rear glove compartment cover 38. When tabs 46 and 48 are pulled apart, they will break lower glove compartment seal 44, left glove compartment seal 40 and right glove compartment seal 42, separating front glove compartment cover 36 from rear glove compartment cover 38 and exposing glove 32 therein. Front glove compartment cover 36 and rear glove compartment cover 38 can be peeled back along the separable seals to upper glove compartment seal 28 which also under force will separate until front glove compartment cover 36 and rear glove compartment cover 38 are only attached around wristband 31 of the interior of sleeve 34 of glove 32 at glove attachment member 30 which is a stronger releasable attachment member than the other compartment edge seal members as described above. With extra force one can then remove front glove compartment cover 36 and rear glove compartment cover 38 from glove attachment member 30 and if, as in the embodiment disclosed, front glove compartment cover 36 is integrally formed in one piece with front entry cover 18 and likewise rear glove compartment cover 38 is integrally formed as one piece with rear entry cover 20, those elements can also be torn away from the glove at glove attachment member 30. When front cover member 17, which includes front entry cover 18 and front glove compartment cover 36, and rear cover member 19 which includes rear entry cover 20 and rear glove compartment cover 38, are torn away from glove attachment member 30, the glove is then totally separated from the front and rear cover members, and sleeve 34 can be rolled up the arm of the user. The glove is then ready for use.

It is often desirable for wearers of sterile gloves to be able to handle other non-sterile materials. The user of the glove of this invention can handle such non-sterile material while wearing the front and rear covers over the glove as they can be of a thin, flexible material and when the wearer needs to use the sterile glove for operative procedures and the like, the wearer can quickly remove the cover members as described above, exposing the glove at the point of use keeping the glove sterile and free of contamination. This glove can also be used to help carry material from one environment to another and afterwards after removal of the cover to expose the sterile glove, the glove can be used when sterile conditions are necessary. Thus the glove of this invention can serve dual purposes, both with the cover on as it is being used under non-sterile conditions since the thin plastic will not significantly interfere with broad hand movements, and yet when the sterile glove is needed, the packaging can be removed to allow for fine hand movements for operative procedures and the like.

Material that is suitable for the entry cover and glove compartment cover can be thin, clear plastic flexible sheet sealed around its edges with a seal that is easily separable upon pulling apart of the tab members as described. The seals around the perimeter of the entry compartment and the glove compartment can be of rubber adhesive or equivalent including heat sealing and would be weaker than the seal formed at glove attachment member 30 around the periphery of the glove which design would allow one to insert one's hand into the glove during periods when one wished to have the covering on the glove while in a state before the needed use of the sterile glove was indicated. The material covering the glove can, in some embodiments, have color detection means on the inside to easily detect whether the glove had been opened at some previous time which opening would compromise the glove's sterility.

Figure 2:
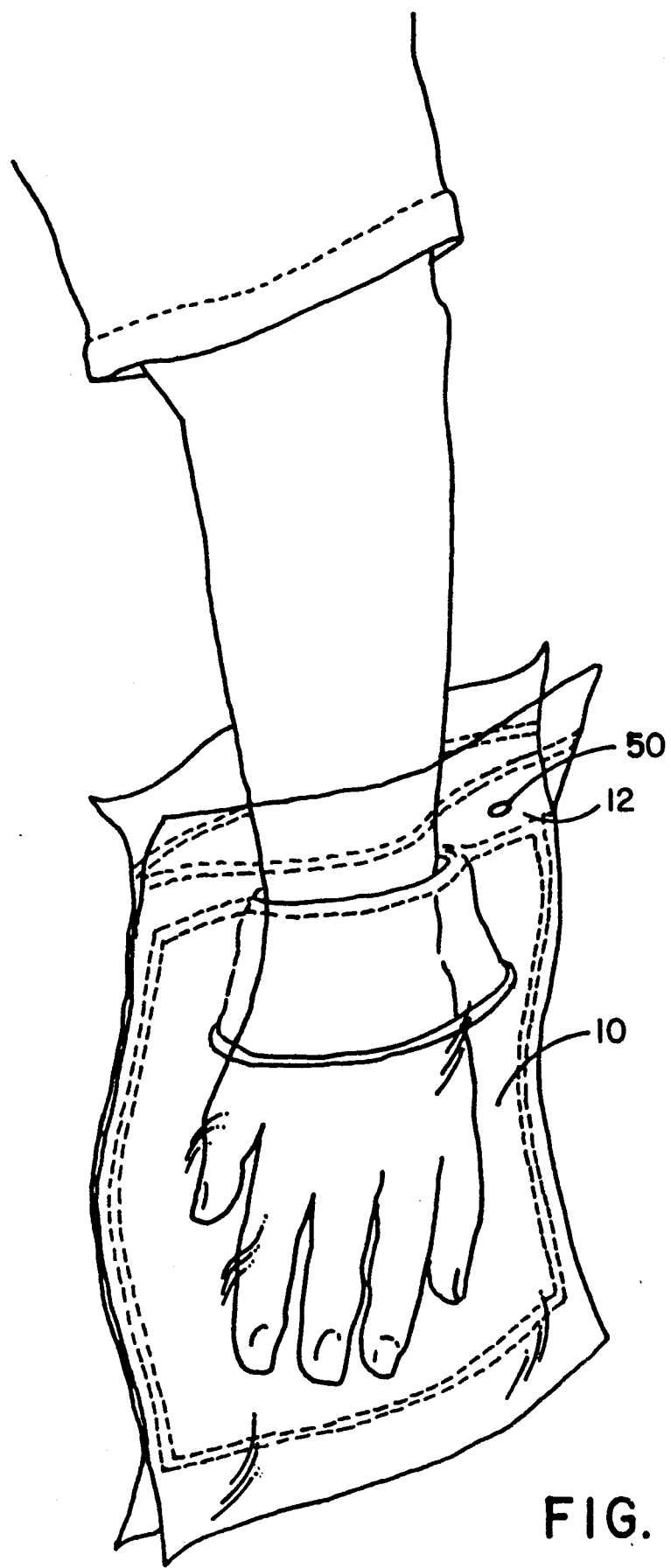
FIG. 2 illustrates a perspective view of the glove with the entry compartment open and the user's hand inserted therein.

In some embodiments chemical components can be added within the upper entry compartment to facilitate hand insertion into the glove such as powders and the like in addition to germ-inhibiting agents which can help control any contamination. Within the glove compartment can be placed viral or germ-inhibiting agents, viricides, germicides, antiseptic solutions, and the like to coat the glove as desired in particular situations. An area or aperture 50 in entry compartment 12 can be provided as seen in FIG. 2 to insert or inject chemical components into the compartments depending on what result is desired.

Although the glove compartment and upper entry compartment are shown as being rectangular in shape, it should be noted that in other shapes and configurations such as angular or rounded can be utilized depending upon the user's requirements.

As mentioned above, glove attachment member 30 has a greater resistance to tearing than the seals between the front and rear compartment covers to prevent accidental overpeeling of the tabs when one is merely trying to enter one's hand into the glove without exposing the glove to the environment. The material of the compartment covers also can have stretchable properties to assist in the insertion of the user's hand and to help in the use of the glove when the glove compartment cover is in place. The hermetically sealed compartments are designed to keep the glove sterile while performing multiple functions. The sealing of the front and rear covers can be done with adhesives or other means that are compatible with the medically intended uses of the glove and compatible with any materials contained with the gloves. It is felt that the glove of this invention will be especially helpful under conditions where the prevention of contamination spreading from one area to another is of concern.

Although the present invention has been described with reference to particular embodiments, it will be apparent to those skilled in the art that variations and modifications can be substituted therefor without departing from the principles and spirit of the invention.

I claim:

1. A combination glove and packaging comprising;
a glove member having a wrist area, a body area, fingers and a sleeve, said sleeve folded forward over the body of said glove member, said glove member with said sleeve folded forward having a top and a bottom;
a front cover member having a top and a bottom, said front cover member disposed over the top of said glove member;
a rear cover member having a top and a bottom, said rear cover member disposed at the bottom of said glove member;
a releasable upper glove compartment seal extending near the top of and between said front cover member and said rear cover member from said wrist area of said glove member, said upper glove compartment seal extending to join said front cover member to said rear cover member, said upper glove compartment seal dividing said front and rear cover members into an upper entry compartment having left front and rear sides and right front and rear sides and a lower glove compartment having a top and a bottom and left and right sides;
a left seal attaching the left front side of said upper entry compartment to the left rear side of said upper entry compartment;
a right entry seal attaching the right front side of said upper entry compartment to the right rear side of said upper entry compartment; an upper entry compartment seal extending between said left entry seal and said right entry seal, said upper entry seal positioned to leave portions of said front cover member and rear cover member unattached to form a front entry tab and a rear entry tab respectively, a lower glove compartment seal extending between said front cover member and said rear cover member near the bottom of said glove compartment beneath the fingers of said glove member;

a left glove compartment seal and right glove compartment seal extending respectively from the left and right sides of said lower glove compartment seal up to said upper glove compartment seal, hermetically sealing said glove compartment area with portions of said front cover member and rear cover member extending unattached below said lower glove compartment seal to form separate front glove compartment tab and rear glove compartment tab respectively, said seals being of the type which are separable by peeling; and a glove attachment member extending around the perimeter of the interior of said sleeve of said glove member at its junction with said upper glove compartment seal, said glove attachment member possessing greater retentive properties than said upper glove compartment seal, such structure adapted to have said upper entry compartment seal and left and right entry seals first separated by pulling apart said front entry tab and rear entry tab along the upper entry seal and left and right entry seals down to said upper glove compartment seal to open said upper entry compartment for insertion of the user's hand through said upper entry compartment into said glove member and when desired, for said front glove compartment tab to be separated from said rear glove compartment tab to separate said lower glove compartment seal and left and right glove compartment seals to peel the front and rear covers back up to said upper glove compartment seal, exposing said glove member with the user's hand therein, said front and rear cover members to be further separated from said glove attachment member at said glove member by further pressure to expose said glove member for use in its sterile mode, such packaging further utilizable while said glove member is contained within said glove compartment for uses suitable therefor while still maintaining said glove member in a sterile condition.

2. The combination glove and packaging of claim 1 further including selected chemical compounds contained within said upper entry compartment and lower glove compartment.

3. The combination glove and packaging of claim 2 further including means to gain access into said upper entry compartment for placement of such chemical compounds therein.

* * * * *